United States Patent [19]
Prahl

[11] Patent Number: 5,007,938
[45] Date of Patent: Apr. 16, 1991

[54] ARTIFICIAL FOOT FOR A LEG PROSTHESIS

[75] Inventor: Gregor M. Prahl, Rullstorf, Fed. Rep. of Germany

[73] Assignee: IPOS GmbH & Co. KG, Fed. Rep. of Germany

[21] Appl. No.: 394,093

[22] Filed: Aug. 15, 1989

[30] Foreign Application Priority Data

Jul. 8, 1989 [DE] Fed. Rep. of Germany ... 8908356[U]

[51] Int. Cl.$^5$ .................................................. A61F 2/66
[52] U.S. Cl. ........................................................ 623/55
[58] Field of Search .......................... 623/53, 54, 55, 56

[56] References Cited

U.S. PATENT DOCUMENTS

| | | | |
|---|---|---|---|
| 2,475,372 | 7/1949 | Catranis | 623/54 |
| 3,890,650 | 6/1975 | Prahl | 623/55 |
| 4,328,594 | 5/1982 | Campbell et al. | 623/53 |
| 4,721,510 | 1/1988 | Cooper et al. | 623/53 |
| 4,892,553 | 1/1990 | Prahl | 623/55 |

FOREIGN PATENT DOCUMENTS 1250286  8/1986  U.S.S.R. .............................. 623/53

Primary Examiner—Randall L. Green
Assistant Examiner—David H. Willse
Attorney, Agent, or Firm—Stanger, Michaelson, Spivak & Wallace

[57] ABSTRACT

Within its plantar area, the artificial foot for a leg prosthesis is provided with a plate-shaped reinforcing member (10) embedded in the molded foot part. The member 10 includes two superimposed upper and lower leaf springs (15a, 15b) possessing different lengths, between which a carbon fiber-reinforced plastic leaf spring (18) is disposed extending. The latter extends into the ball of the foot area and is offset at the front end. Sliding inserts (17a, 17b) of polyethylene and each face of the plastic leaf spring and between the upper and lower leaf springs produce a constant metatarsal elasticity even during continuous stress.

19 Claims, 2 Drawing Sheets

ARTIFICIAL FOOT FOR A LEG PROSTHESIS

BACKGROUND OF THE INVENTION

The present invention relates to an artificial foot for a leg prosthesis consisting of a foamed plastic molded foot part with a plate-shaped reinforcing member embedded within its plantar area that is provided with at least two approximately equally long superimposed leaf springs with an elastic distance piece and sliding insert of polyethylene possessing a high slidability and which, within the area of the ball of the foot, is constructed with an offset extending in the same manner as the ball of the foot for supporting the foot rolling function and with—serving in each case as elastically yielding springing—a forefoot core and a function core consisting of a tongue disposed within the calcaneal area, the function core and the reinforcing member being rigidly interconnected.

Polyurethane foamed plastic has been used as material for artificial feet for a long time; it possesses the advantage of a low weight.

In order to enable the artificial foot to approximately perform the function predetermined in a natural foot for instance, in the U.S. Pat. No. 3,335,428, a leg prosthesis foot part has been proposed which is molded from resilient plastic materials of differing hardness.

Furthermore, from the DE-PS No. 354,246, an artificial foot is known in which, within the plantar area of the artificial foot, a metal strip is embedded. This artificial foot is intended to render possible the taking of long strides for a foot or leg amputee since the taking of big strides gives rise to the oblique change of position of the lower leg toward the rear, thus the yielding of the heel of the foot resting on the ground with its entire undersurface. It is further intended to bring about the easy straightening up again of the lower leg without that the same exceeds the vertical position, while the forward shifting of the body weight and the raising of the heel is intended to be rendered possible by the normal flexibility of the metatarsal and dactylar portion of the artificial foot. This flexibility is intended to be achieved by the embedding of a spring plate passing through the plantar and calcaneal portion. In order to now be able to bring about the oblique change of position toward the rear of the lower leg, this known embodiment of an artificial foot provides a connection between the rigid lower leg and the spring plate, in which the lower leg moves rearward from its upright position in the manner of a cradle and, when shifting the body weight forward, returns once more into the first position. This seesaw motion takes place due to the circumstance that the cuneiformly tapering, rigid lower leg is seated in a so-called saddle, one slope of which is formed by the instep of the artificial foot, the counterslope of which is formed by a branch of the leaf spring. For a further shock absorption, a compressible wedge cushion, e.g. of soft rubber, is located between the branch and the actual spring plate. In order to avoid the occurrence of undesired noises when the front wedge surface on the lower leg strikes against the foot, the forefoot or metatarsus consists of a flexibly or readily compressible, but at any rate sound-absorbent, mass, preferably felt. The abutment surface of the lower leg, too, is covered with a cap of this material. In this artificial foot, a steel spring having spring properties is used which extends as far s into the forefoot. However, the important elasticity differences between metatarsus and forefoot have not been taken into constructional consideration in this case. The steel spring employed does not render a natural rolling possible; in addition, the connecting problems between the different materials within the elastic areas are not solved from a structural view.

Moreover, from the DE-PS No. 361 972, there is known an artificial foot with a longitudinal spring system consisting of several leaf springs that are stepped relative to each other, said leaf springs being fastened with their rearward ends to the lower side of a rigid block forming the rear foot portion, but which is separated from the sole by an intermediate layer, while the front ends extend downwardly in an appropriate double bend and press directly on the sole which is expediently protected by a protective plate. In this artificial foot, too, an attempt is made to control the movements of the foot by means of a metal spring, however, it does not allow any mobility or flexibility within the metatarsophalangeal area.

In an artificial foot for leg prostheses known from the U.S. Pat. No. 2,556,525, a rigid but flexible plastic portion is embedded in an external foamed plastic molded part that extends across the entire length of the foot, while a metal insert of spring steel is embedded in said rigid but flexible plastic part. Even if an internal, partially flexible plastic part with a metal insert of spring steel were to be employed in this known artificial foot, it is not possible in this artificial foot to lay the rolling function onto the trisectional line predetermined by nature. Incidentally, the metal insert is also run up to the tip of the foot.

Despite the use of a flexible plastic part and of a metal insert of spring steel, an adequate mobility within the metatarsophalangeal articulation, as exists in nature, is not possible. The important flexing in the metatarsophalangeal joint has not been taken into consideration in this known embodiment and, on account of the constructional configuration, is not possible either.

That is why, in order to provide an artificial foot for leg prostheses with a rolling resistance of high resilience predetermined over a relatively long period and a flexing possibility in the metatarsophalangeal articulation, the artificial foot described in the beginning has been proposed in the DE-PS No. 23 41 887. In this artificial foot, the forefoot elasticity is ensured by the use of a homogeneous Vulkollan (elastomer) constituent, that is to say that, in the forefoot, a restoring or returning resilience is taken into account which went far beyond the padding effects formed until then. However, it had not been possible to functionally utilize the advantages of said restoring resilience in its physical influence value on the gait image.

In order to ensure a great metatarsal elasticity up to a maximum rolling moment of 120 Nm even in the case of a continuous stress of up to 3 million load alternations without having to dispense with the advantages of the artificial foot known from the DE-PS No. 23 41 887, it is proposed in the DE-Gbm No. 88 04 228.6, that the reinforcing member consist of at least two approximately equally long, superimposed leaf springs which are configured in such as way as to correspond to the rolling profile of the foot. This foot possesses a great mobility in the metatarsophalangeal joint, and an elastic yielding springing both in the forefoot as well as within the calcaneal area, the rolling resistance being predetermined so as to be unchangeable over a relatively long period. Over and above that, a simple adaptation to different heel heights is possible and a maximum of wearing comfort is ensured for the person using the artificial foot without any readjustment function for retaining a uniform foot rooling function becoming necessary. By supporting the metallic reinforcing member in the calcaneal portion of the molded foot part, an increased strength of the molded foot part is achieved without which the requisite resilient and yielding springing means in the forefoot and within the calcaneal area are adversely affected. The simple adaptation to different heel heights is possible by merely changing the tongue disposed in the calcaneal portion of the molded foot part without an alteration of the entire function core being necessary for this in order to achieve an adaptation to different heel heights.

This construction makes it possible in particular that, by means of the resiliently constructed forefoot and metatarsal areas, kinetic energy is absorbed and stored and, in the relief of the rearward movement, is once more fed into the prosthesis in the form of energy being released. This recycling of released kinetic energy into the prosthetic system does demonstrably result in a clear energy relief during the locomotion of the patient. Furthermore, it is now possible to do without ankle joints in the artificial foot, as a result of which a loss of energy arising in the ankle joints due to friction is avoided and the stored energy can be fully utilized again as return energy. The artificial foot is highly resilient within the forefoot and metatarsal area and is capable of absorbing a maximum rolling moment of 120 Nm. This maximum rolling load also determines the dimensioning of the springs.

SUMMARY OF THE INVENTION

It is the object of the present invention to improve the artificial foot stated in the beginning to the effect that, with a rolling moment of up to 140 Nm, and in continuous stress (load alternations of up to 10 million), an at least uniform metatarsal elasticity is achieved preferably with a reduced weight.

This technical problem is solved by the combination of the features indicated in claim 1. The carbon fiber-reinforced synthetic resin leaf spring has produced much more favorable load alternation figures under test conditions.

Further developments of the invention are described in the claims 2 to 16. In particular, by constructing the upper and lower metallic leaf springs so as to be much shorter, it is possible to reduce the weight to a significant degree. In a preferred embodiment, the resilient part of the artificial foot is constructed as detailed in the following:

The carbon fiber-reinforced synthetic resin leaf spring extends as far as into the ball of the foot area and lies between an upper titanium spring which terminates in the middle of the foot, and of a lower titanium leaf spring which is constructed so as to be substantially shorter than the upper spring. Between the springs, a sliding insert of polyethylene is disposed in each case. This resilient portion is, as is known in principle according to the state of the art, vulcanized into the foot. In the spring construction explained, the weight reduction, in comparison with the known state of the art, is approximately 40%.

BRIEF DESCRIPTION OF THE DRAWINGS

An embodiment of the invention will be explained in the following with the aid of the drawings. Thus

DETAILED DESCRIPTION OF THE PREFERRED EMBODIMENT

Figure 1:
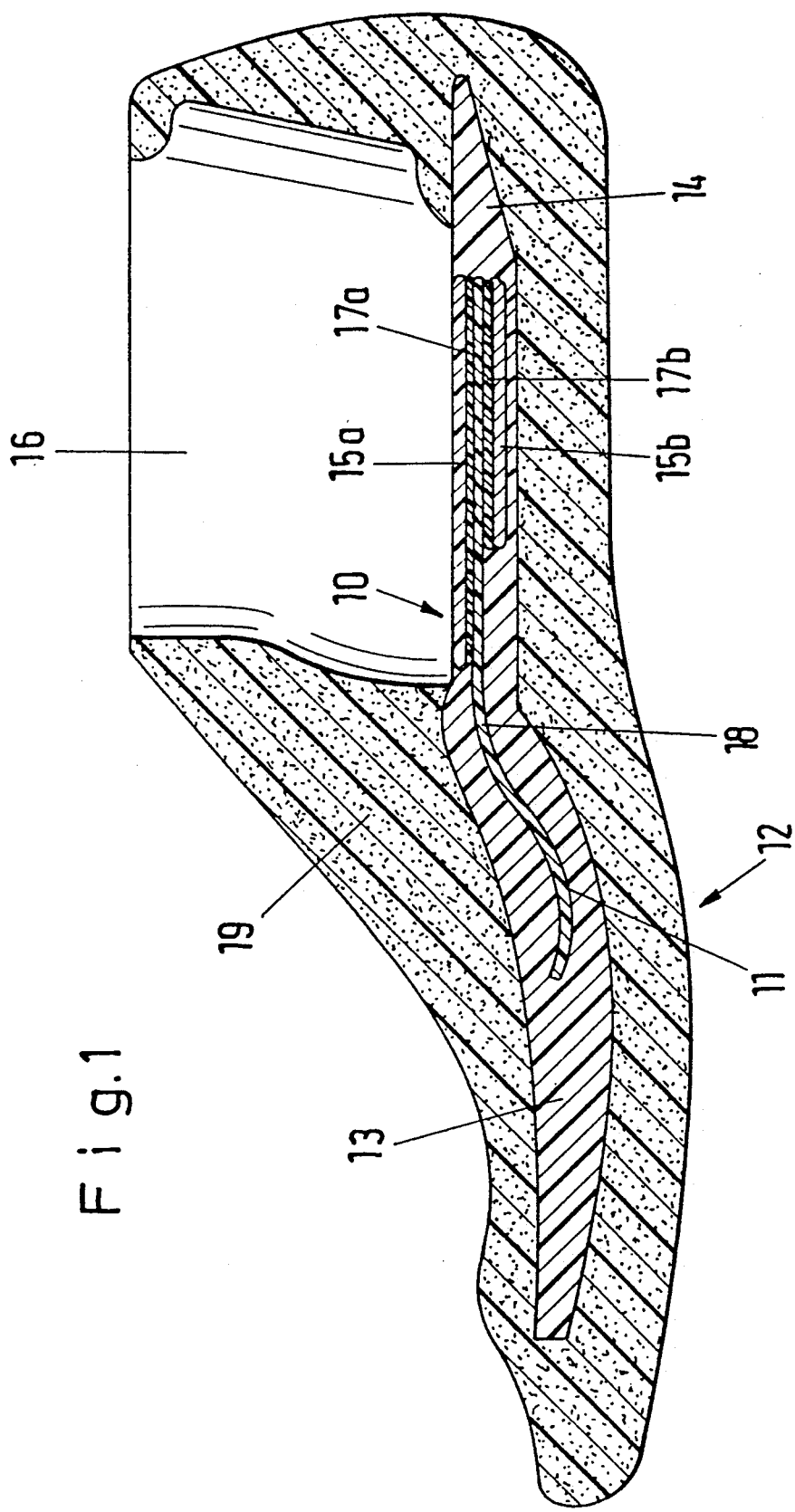
FIG. 1 shows a section through the artificial foot.

The artificial foot depicted in FIG. 1 is provided with a reinforcing member 10 with a downwardly directed offset 11 within the area of the ball of the foot 12, which is shaped in correspondence to the rolling profile of the artificial foot. The reinforcing member 10 is embedded in the same manner in a forefoot core 13 as in a tongue 14 located within the calcaneal area. The reinforcing member 10 is subdivided into an upper leaf spring 15a, a sliding insert 17a of polyethylene as distance piece to the main spring, a carbon fiber-reinforced plastic leaf spring 18, which extends as far as into the area of the ball of the foot and which is bent at the front end, a further sliding insert 17b, as well as a lower titanium spring 15b which terminates the reinforcing member in the downward direction. The function core consisting of the reinforcing member 10, the forefoot core 13 and the tongue 14 are embedded in a foamed plastic molded foot part 19 which has a cavity 16 in the rearward portion that is taken up to the reinforcing member 10, i.e. the upper titanium leaf spring 15a, and in which articulations or rigid fasteners can be screwed directly to the reinforcing member 10.

Figure 2:
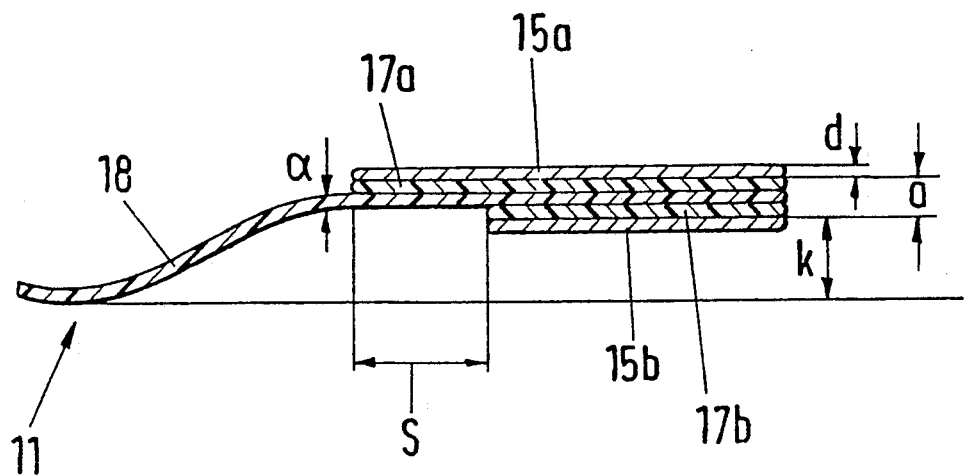
FIG. 2 shows a side view of the reinforcing member.
Figure 3:
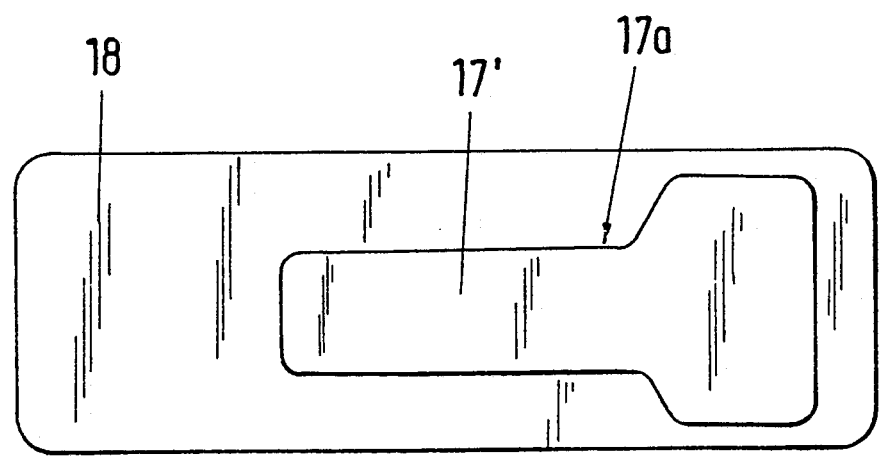
FIG. 3 shows a top view of the carbon fiber-reinforced synthetic resin leaf spring with an elastic sliding insert placed thereupon.

The downwardly bent offset 11 is constructed in such a way that the rolling function is laid onto the front trisectional line (metatarsophalangeal line) provided by nature. In this connection, onto the offset 11 of the reinforcing member 10, a forefoot core 13 consisting of an elastomer is vulcanized which, in its lower terminal line, corresponds to the external shape of the ball of the foot. This forefoot core is completely resistant to aging due to the structure being embedded in foamed plastic so that the rolling resistance can be unchangeably predetermined over relatively long periods. A tongue 14 of an elastomer is likewise attached by vulcanization in the calcaneal section in order to strengthen the reinforcing member 10. The construction of the reinforcing member 10 more particularly concerning the invention can be seen in detail in FIGS. 2 and 3. The metatarsal construction consists in this case of an upper titanium leaf spring 15a extending approximately into the middle of the foot, a carbon fiber-reinforced synthetic resin leaf spring 18 which is offset at the front end and which projects approximately up to the ball of the foot area, and a lower leaf spring 15b. Between the leaf springs 15a and 15b and the carbon fiber-reinforced synthetic resin leaf spring 18, sliding inserts 17a and 17b are arranged. The upper metallic leaf spring 15a projects over the lower metallic leaf spring 15b by the dimension s, which amounts to at least 15 mm. As can be seen from FIG. 3, particularly the leaf spring 18 is constructed so as to be essentially rectangular in shape, while the distance piece 17a is T-shaped, the tongue-shaped leg of which extends up to the middle of the foot. This sliding insert prevents a contact of the synthetic resin leaf spring 18 with the upper titanium leaf spring 15a. At the same time, the sliding inserts 17a and 17b have a sound absorbing effect and allow a control of the elastic force to be maximally absorbed. The greater the distance a between the metallic leaf springs, or between a leaf spring of titanium and a synthetic resin leaf spring 18, the greater the maximum stability under the load of the artificial foot will be. However it is just as possible to employ sliding inserts 17a and 17b of polyurethane, especially a cross-linked polyurethane elastomer. Polyurethane possesses a strong abrasion resistance so that at all times a uniform rolling effect is ensured. To this is added the great automatic returning capacity from a deformed position to the initial position. The foot core 13 and the tongue 14 consist of polyurethane, particularly a cross-linked polyurethane elastomer known by the trade name of Vulkollan. It is also possible to employ polyurethanes which are obtained by the conversion of diisocyanates, which are known by the trade name of Desmodur, according to the polyisocyanate-polyaddition process. Isocyanate types that are frequently employed in said process are TDI, MDI and HDI. Above all, triisocyanates and, by way of example, polyisocyanates are used for strongly cross-linked polyurethanes. Here, too, the high slidability property is exploited.

The embodiments described possess the advantage that horizontal displacements between the metallic leaf springs within the forefoot area, which up till now had to be prevented by specially constructed sliding inserts, are unable to take place from the outset. Over and above that, it is possible to achieve a great saving in weight with the present construction. Owing to the distance k between the plane determined by the rear leaf spring plane and the offset, relatively large spring ranges are achieved which, in part, render the employment of articulations superfluous due to their functionally great dorsal flexion. At the same time, a large range of energy being released is produced in the elastic recovery and can be fed back into the prosthesis system.

The leaf spring construction at a minimum weight is capable of standing up to a high rolling load, operates completely noiselessly and is distinguished by large spring ranges. Due to the combination of the titanium leaf springs and the carbon fiber-reinforced synthetic resin leaf spring in connection with the sliding inserts, the invention is superior to other artificial foot constructions known from the state of the art.

What is claimed is:

1. Artificial foot for a leg prosthesis, comprising a foamed plastic molded foot part and a plate-shaped reinforcing member embedded within its plantar area
said reinforcing member including at least two superimposed upper and lower leaf springs and a spacer in the form of an elastic sliding insert of polyethylene possessing a high degree of slidability between said leaf springs, an offset portion within the area of the ball of the foot and extending in the manner of a ball of the foot for supporting a foot rolling function, elastically yielding springing means having a forefoot core and a function core disposed within a calcaneal area and forming a tongue, the function core and the reinforcing member being rigidly interconnected.
characterized in that, a carbon fiber-reinforced synthetic resin leaf spring is disposed between said upper and lower leaf springs, and said synthetic resin leaf spring is configured in conformity with the rolling profile of the foot and extends as far as into the area of the offset portion.

2. Artificial foot according to claim 1, characterized in that the upper leaf spring is essentially planar, and in that its end pointing toward the tip of the foot extends approximately as far as to the middle of the foot.

3. Artificial foot according to claim 1, characterized in that the lower leaf spring is constructed so as to be shorter than the upper leaf spring.

4. Artificial foot according to claim 3, characterized in that the lower and the upper leaf springs, within the rear are, terminate approximately in the same vertical plane.

5. Artificial foot according to claim 1, characterized in that, a second elastic sliding insert is disposed between one of the upper and lower leaf springs and the carbon fiber-reinforced synthetic resin leaf spring, said upper and lower leaf springs being metallic, said leaf springs being substantially planar.

6. Artificial foot according to claim 1, characterized in the upper and lower leaf springs are composed of titanium, a high-strength titanium-aluminum alloy or the like.

7. Artificial foot according to claim 1, characterized in that at least two of the leaf springs are of equal thickness.

8. Artificial foot according to claim 1, characterized in that the upper leaf spring projects over the bottom leaf spring in the direction of the tip of the foot by at least 15 mm.

9. Artificial foot according to claim 1, characterized in that any one of the reinforcing member and the upper and lower leaf springs and the carbon fiber-reinforced synthetic resin leaf spring, in a top view projection, is essentially rectangular and possesses rounded off corners and edges.

10. Artificial foot according to claim 5, characterized in that the second sliding insert between the one of the upper and lower leaf springs and the carbon fiber-reinforced synthetic resin leaf spring is composed of material possessing a high degree of slidability.

11. Artificial foot according to claim 10, characterized in that the distance between the upper and lower leaf springs within the calcaneal area is at least 3 mm.

12. Artificial foot according to claim 10, characterized in that the sliding inserts have a thickness of 1 mm.

13. Artificial foot according to claim 10, characterized in that the sliding inserts within the calcaneal area, are substantially T-shaped and a tongue shaped leg is directed toward the tip of the foot, such that any one of the upper and lower leaf springs and the carbon fiber-reinforced synthetic resin leaf spring projects beyond the sliding inserts on all sides.

14. Artificial foot according to claim 1, characterized in that any one of the upper and lower leaf springs and the carbon fiber-reinforced synthetic resin leaf spring is embedded in the forefoot core and the tongue, both of which are fabricated from polyurethane.

15. Artificial foot according to claim 1, characterized in that the carbon fiber-reinforced synthetic resin leaf spring extends from the calcaneal area into the metatarsal area and is constructed so as to be essentially planar, and in that the offset within the ball of the foot area extends at least 15 mm deeper than said leaf springs.

16. Artificial foot according to claim 1, characterized in that the carbon fiber-reinforced synthetic resin leaf spring, within the area of the offset (11), is at least as wide as within the calcaneal area.

17. Artificial foot according to claim 1, characterized in that the carbon fiber-reinforced synthetic resin leaf spring extends 16 mm to 21 mm deeper than said upper and lower leaf springs.

18. Artificial foot according to claim 1, characterized in that at least two of the leaf springs have a thickness of substantially 2.7 mm.

19. Artificial foot according to claim 5, characterized in that the second sliding insert between the one of the upper and lower leaf springs and the carbon fiber-reinforced synthetic resin leaf spring is composed of molecular polyethylene.

* * * * *